April 16, 1968 C. R. GIBSON Plant Pat. 2,803
APPLE TREE
Filed Jan. 6, 1967
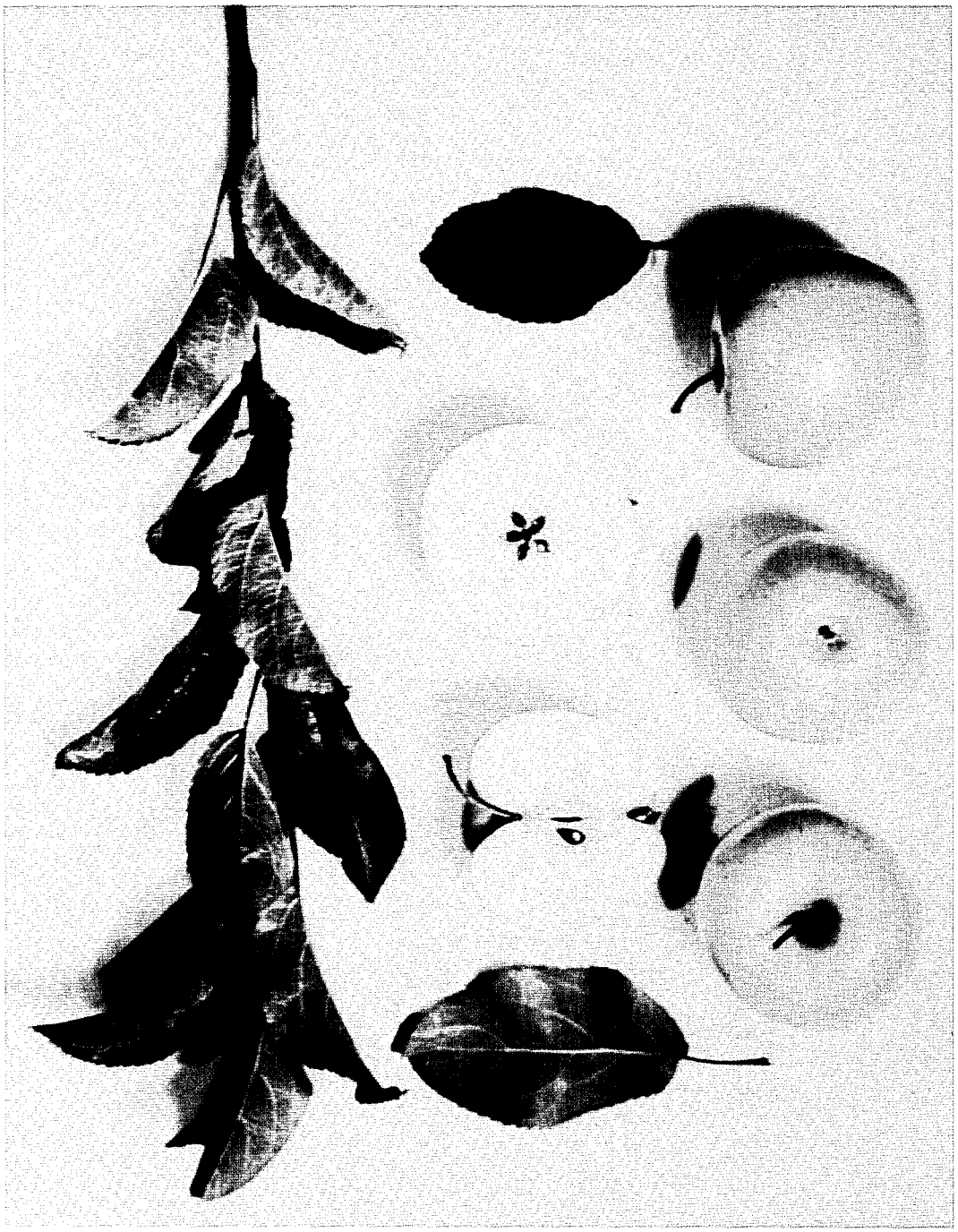
Inventor.
Carl R. Gibson
By: Robb & Robb
Attorneys.

United States Patent Office

Plant Pat. 2,803
Patented Apr. 16, 1968

2,803
APPLE TREE

Carl R. Gibson, Evans City, Pa., assignor to Hill Top Orchards and Nurseries, Inc., Hartford, Mich.

Filed Jan. 6, 1967, Ser. No. 607,866
1 Claim. (Cl. Plt.—35)

The present invention relates to a new and distinct variety of apple tree which was discovered by me as a whole tree sport on my cultivated property in Forward Township, Butler County, Pa.

At the time of my discovery aforesaid, I was growing an orchard of the apple variety known as "Golden Delicious" (unpatented), or sometimes called "Yellow Delicious." One tree in this orchard attracted my particular attention when it was at the age of about four years, because of its outstanding characteristics which were materially different in a number of respects from the normal characteristics of the "Golden Delicious" variety which were growing under the same conditions adjacent thereto. Close examination of this particular tree and subsequent observations thereof and of its progeny which I asexually reproduced therefrom by both grafting and budding, on my own property and elsewhere under my control and on my behalf in the States of Pennsylvania and Michigan, have convinced me, as well as qualified experts, that my new variety originated as a whole tree sport of "Golden Delicious" and was definitely distinguished therefrom and from all other varieties of which I am aware, as evidenced by the following unique combination of characteristics which are established and come true through succeeding propagations:

(1) A vigorous, uniform, very healthy and winter-hardy habit of growth, with proven ability to survive without injury cold temperatures as low as −25° F.;

(2) Foliage having its upper leaf surface more rugose and distinctly more pubescence on the under surface, with more prominent veins, but being less deeply incised and with more distinct apexes than the foliage of "Golden Delicious";

(3) A more consistent annular fruit bearing habit than "Golden Delicious," which tends to be bi-annual;

(4) A stronger tendency to a spur type of growth;

(5) Fruit resembling that of "Golden Delicious" but being larger, longer and more conic in shape, with more pronounced lobes, firmer flesh, and a tendency of the skin to acquire a more pronounced red blush than "Golden Delicious"; and (6) A marked resistance to and freedom from russet under relatively high humid conditions which prevail in the eastern half of the United States, with a consequent commercial capability of greater fresh market utilization of the fruit.

The accompanying drawing shows typical specimens of the foliage and fruit of my new variety of apple tree as depicted in color as nearly true as it is reasonably possible to make the same in a color illustration of this character, certain of the fruit speciments being shown in both elevation and in plan to disclose the exterior details thereof, and other fruit specimens being shown in both longitudinal and transverse cross-section to disclose the interior details.

The following is a detailed description of my new variety, with color terminology in accordance with the Nickerson Color Fan, except where general color terms of ordinary dictionary significance are obvious:

Locality where grown and observed: Evans City, Pa.

Dates of first and last pickings: Usually the same as for "Golden Delicious."

Tree: Medium size and vigor; upright-spreading form; rather dense, but not excessively so, with a round-topped appearance; moderately rapid grower; hardy to winter temperatures as low as −25° F. without injury; above average producer; consistently regular annular bearer.

*Trunk.*—Medium size; medium smooth.

*Branches.*—Medium size, smoothness and branching habit, with tendency to a greater number of lateral fruit spurs than is normal for "Golden Delicious." Color—predominantly tannish-gray.

*Lenticels (on one-year bark).*—Numerous; conspicuous; raised; mostly round. Color—from light tan to whitish.

*Leaves.*—Narrow; strongly U-folded; ovate; rather thick; rugose; apex acutely drawn and twisted. Color—rather dark green. Length—about 4 inches. Width—from about 1½ inches to 1¾ inches. Margin—finely serrate. Petiole—long (about 1¼ inches to 1½ inches); medium thickness.

Flowers: Similar to those of "Golden Delicious" and about the same blooming period.

Fruit:

*Maturity when described.*—Eating hard; about the same ripening period as "Golden Delicious."

*Size.*—Axial diameter—averages about 3 inches. Transverse diameter—averages from about 2⅞ inches to 3 inches.

*Form.*—Uniform; symmetrical; regular; conic.

*Cavity.*—Symmetrical; acute. Breadth—averages 1¾ inches. Depth—averages from ¾ inch to 1 inch. Markings—characteristic greenish-tan russeting in stem cavity.

*Basin.*—Symmetrical; abrupt; narrow; furrowed; with moderate pubescence on the calyx lobes.

*Stem.*—Slender; glabrous; with 2 very inconspicuous bracts. Length—from 1 inch to 1½ inches.

*Calyx.*—Variable from closed to moderately open; persistent; acuminate to ⅜ inch long; lobes are erect, connivent and pubescent on both the inner and outer surfaces.

*Eye (calyx tube).*—From closed to partly open.

*Skin.*—Thick; tender; rather smooth; dull. Dots—obscure; many; small; even submerged (on apical half of fruit) ruptured on basal half-stem end; circular; more numerous on the apical half. color—greenish-cream.

*General color effect.*—Predominantly yellow, with many fruit having a light reddish-blush on the shoulder; average cheek color varies between Vivid Greenish-Yellow, Plate 7.5Y 8/12 and Vivid Yellow, Plate 5Y 8/12.

*Ground color.*—From greenish to light yellowish-green.

*Bloom.*—None.

*Scarfskin.*—A few flecks of whitish color.

*Flesh.*—Juicy. Color—white. Texture—firm; coarse; crisp. Flavor—subacid; sweet; rich. Aroma—wanting. Quality—excellent (best).

*Core.*—Median. Bundle area—from medium to small; nearly cordate. Halves of core—equal. Bundles—inconspicuous; in one whorl. Color—green. Alternate bundle—reaches the tube above the stamens. Core lines—meeting; indistinct. Carpellary area—distinct; small. Calyx tube—pubescent; narrowly cone-shaped; funnel stem—short; about ¼ inch long; entire tube—about ⅝ inch long. Styles—present; united. Stamens—persist; in one obscure median whorl. Axillary cavity—wanting. Seed cells—abaxile; open. Cell walls—thin; tough; length—½ inch; width—½ inch. Longitudinal section—broadly obovate; mucronate; with inner surface fissured and tufted. Cross-section—broad.

Seed: Average from 6 to 8 per apple, with 2 being greatest number in one cell.

*Length.*—Average ¼ inch.

*Width.*—Average ⅛ inch.

*Form.*—Acute.

*Color.*—From very dark brown at the hilum to light tan at the opposite end.

Use: Local; dessert; processing.

Keeping Quality: Substantially equal to "Golden Delicious."

Resistance to insects and diseases: Comparable to "Golden Delicious," as determined by comparison with the latter grown under the same conditions in Pennsylvania and Michigan.

I claim:

1. A new and distinct variety of apple tree of the yellow skinned and white fleshed fruit class, substantially as herein shown and described, characterized particularly as to novelty by the unique combination of a vigorous, uniform, very healthy and winter-hardy habit of growth, with proven ability to survive without injury cold tempertures as low as —25° F., foliage having its upper leaf surface more rugose and distinctly more pubescence on the under surface, with more prominent veins, but being less deeply incised and with more distinct apexes than the foliage of "Golden Delicious," a more consistent annular fruit bearing habit than "Golden Delicious" which tends to be biannual, a stronger tendency to a spur type of growth, fruit resembling that of "Golden Delicious" but being larger, longer and more conic in shape, with more pronounced lobes, firmer flesh, and a tendency of the skin to acquire a more pronounced red blush than "Golden Delicious," and a marked resistance to and freedom from russet under relatively high humid conditions which prevail in the eastern half of the United States, with a consequent commercial capability of greater fresh market utilization of the fruit.

No references cited.

ROBERT E. BAGWILL, *Primary Examiner.*